United States Patent
Pop et al.

(10) Patent No.: US 6,710,218 B1
(45) Date of Patent: Mar. 23, 2004

(54) CATALYTIC PROCESS FOR THE PREPARATION OF LIGHT OLEFINS FROM METHANOL IN FLUIDIZED BED REACTOR

(75) Inventors: Grigore Pop, Bucureşti (RO); Rodica Ganea, Bucureşti (RO); Doina Ivanescu, Bucureşti (RO); Rodica Boeru, R-Ploieşti (RO); Gheorghe Ignatescu, R-Ploieşti (RO); Ruxandra Birjega, Bucureşti (RO)

(73) Assignee: Casale Chemicals SA, Lugano-Besso (CH)

( * ) Notice: Subject to any disclaimer, the term of this patent is extended or adjusted under 35 U.S.C. 154(b) by 0 days.

(21) Appl. No.: 09/869,974

(22) PCT Filed: Jan. 11, 1999

(86) PCT No.: PCT/RO99/00001

§ 371 (c)(1),
(2), (4) Date: Oct. 22, 2001

(87) PCT Pub. No.: WO00/41986

PCT Pub. Date: Jul. 20, 2000

(51) Int. Cl.$^7$ .................................................. C07C 1/20
(52) U.S. Cl. ........................ 585/640; 585/638; 585/639
(58) Field of Search .............................. 585/638, 639, 585/640

(56) References Cited

U.S. PATENT DOCUMENTS

| | | |
|---|---|---|
| 3,244,766 A | 4/1966 | Keough et al. |
| 3,702,886 A | 11/1972 | Argauer et al. |
| 3,911,041 A | 10/1975 | Kaeding et al. |
| 3,979,472 A | 9/1976 | Butter |
| 4,025,572 A | 5/1977 | Lago |
| 4,025,575 A | 5/1977 | Chang et al. |
| 4,049,573 A | 9/1977 | Kaeding |
| 4,049,735 A | 9/1977 | Chen et al. |
| 4,062,905 A | 12/1977 | Chang et al. |
| 4,066,714 A | 1/1978 | Rodewald |
| 4,079,096 A | 3/1978 | Givens et al. |
| 4,083,889 A | 4/1978 | Caesar et al. |
| 4,100,219 A | 7/1978 | Rodewald |
| 4,145,315 A | 3/1979 | Rodewald |
| 4,310,440 A | 1/1982 | Wilson et al. |
| 4,328,384 A | 5/1982 | Daviduk et al. |
| 4,374,295 A | 2/1983 | Lee |
| 4,433,189 A | 2/1984 | Young |
| 4,440,871 A | 4/1984 | Lok et al. |
| 4,447,669 A | 5/1984 | Hamon et al. |
| 4,481,376 A | 11/1984 | Wunder et al. |
| 4,486,617 A | 12/1984 | Hoelderich et al. |
| 4,499,315 A | 2/1985 | Garska et al. |
| 4,499,327 A | 2/1985 | Kaiser |
| 4,590,320 A | 5/1986 | Sapre |
| 4,861,938 A | 8/1989 | Lewis et al. |
| 4,873,390 A | 10/1989 | Lewis et al. |
| 4,973,792 A | 11/1990 | Lewis et al. |
| 5,095,163 A | 3/1992 | Barger |
| 5,126,308 A | 6/1992 | Barger et al. |
| 5,290,932 A | 3/1994 | Dingerdissen et al. |
| 5,663,471 A | 9/1997 | Kvisle et al. |
| 5,744,680 A | 4/1998 | Mulvaney, III et al. |
| 5,817,906 A | 10/1998 | Marker et al. |
| 5,912,393 A | 6/1999 | Barger et al. |
| 5,914,433 A | 6/1999 | Marker |
| 5,925,586 A | 7/1999 | Sun |
| 5,952,538 A | 9/1999 | Vaughn et al. |
| 5,972,205 A | 10/1999 | Tsang et al. |
| 6,040,264 A | 3/2000 | Sun et al. |
| 6,046,371 A | 4/2000 | Wu et al. |
| 6,051,745 A | 4/2000 | Wu et al. |
| 6,051,746 A | 4/2000 | Sun et al. |
| 6,121,503 A | 9/2000 | Janssen et al. |
| 6,137,022 A | 10/2000 | Kuechler et al. |
| 6,153,798 A * | 11/2000 | Hidaka et al. .............. 564/479 |
| 6,166,282 A | 12/2000 | Miller |
| 6,207,872 B1 | 3/2001 | Barger et al. |

FOREIGN PATENT DOCUMENTS

| | | |
|---|---|---|
| DE | 26 15 150 A1 | 10/1976 |
| DE | 27 55 299 A1 | 6/1978 |
| DE | 28 30 830 A1 | 1/1980 |
| DE | 29 35 863 A1 | 3/1980 |
| DE | 28 30 787 A1 | 10/1980 |
| DE | 33 00 892 A1 | 7/1984 |
| EP | 0 318 282 B1 | 5/1984 |
| EP | 0 249 915 B1 | 12/1987 |
| EP | 0 357 831 A1 | 3/1990 |
| EP | 0 359 842 A1 | 3/1990 |
| EP | 0 893 159 A1 | 1/1999 |
| GB | 2 127 036 A | 4/1984 |
| WO | WO 86/03694 A1 | 7/1986 |
| WO | WO 86/04577 A1 | 8/1986 |
| WO | WO 93/24430 A1 | 12/1993 |
| WO | WO 97/21652 A1 | 6/1997 |
| WO | WO 97/45196 A1 | 12/1997 |
| WO | WO 98/29370 A1 | 7/1998 |
| WO | WO 98/29519 A1 | 7/1998 |
| WO | WO 98/57912 A1 | 12/1998 |
| WO | WO 99/18055 A1 | 4/1999 |
| WO | WO 99/28277 A1 | 6/1999 |
| WO | WO 99/55651 A1 | 11/1999 |
| WO | WO 99/57087 A1 | 11/1999 |
| WO | WO 00/01643 A1 | 1/2000 |
| WO | WO 00/49106 A1 | 8/2000 |
| WO | WO 00/63144 A1 | 10/2000 |
| WO | WO 00/74846 A2 | 12/2000 |
| WO | WO 00/74848 A1 | 12/2000 |
| WO | WO 00/75072 A1 | 12/2000 |
| WO | WO 01/25150 A1 | 4/2001 |

\* cited by examiner

*Primary Examiner*—Walter D. Griffin
(74) *Attorney, Agent, or Firm*—Sughrue Mion, PLLC

(57) ABSTRACT

Methanol is converted in light molecular olefins $C_2$–$C_4$ with 93–100% degree of transformation and more than 90% selectivity in which more than 80% are ethylene and propylene upon a microspherical catalyst based on SAPO-34 zeolite, with continuous reaction-regeneration in a fluidized bed reactor-regenerator system. Ethylene/propylene ratio is changed in relatively large limits 0.69–1.36, by the modification of reaction temperature and space velocity of the feed.

7 Claims, 3 Drawing Sheets

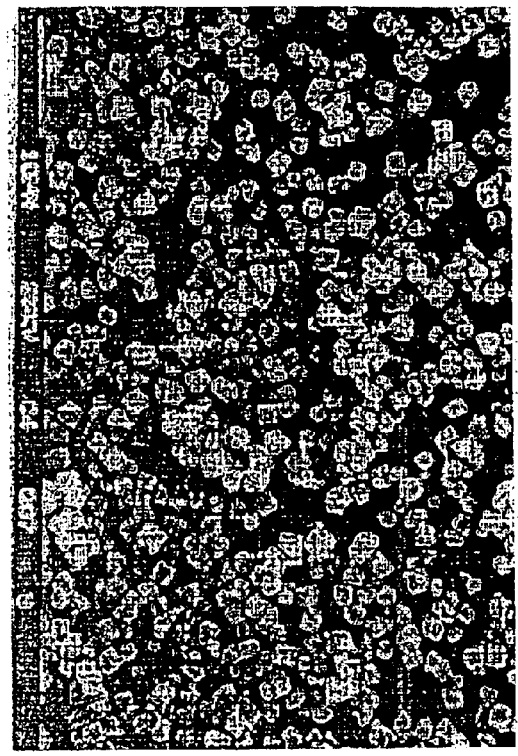
Figure 1. SEM microphotography of Example 1 zeolite

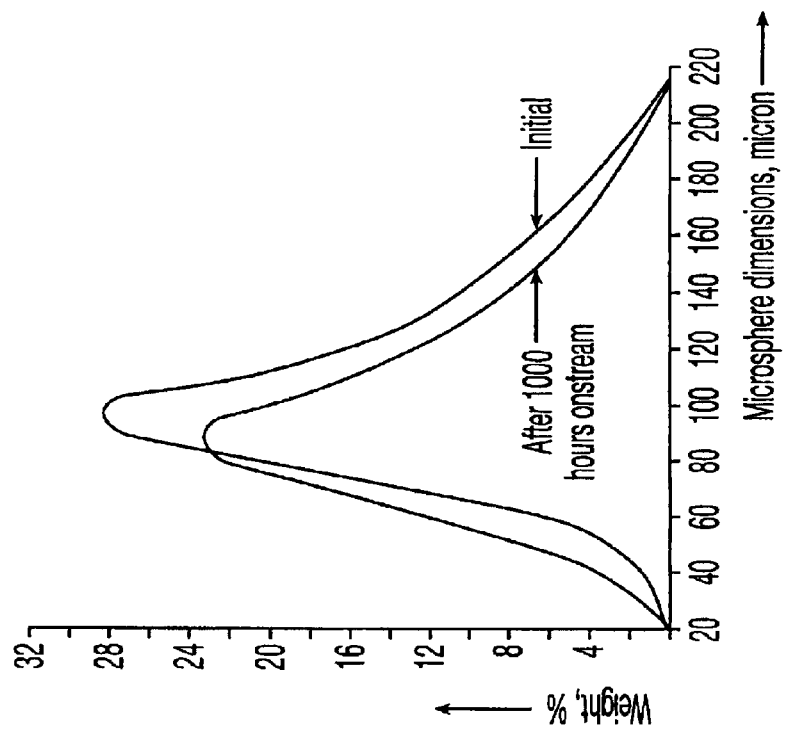
Figure 3. dimension distribution curves of the catalyst, Example 1
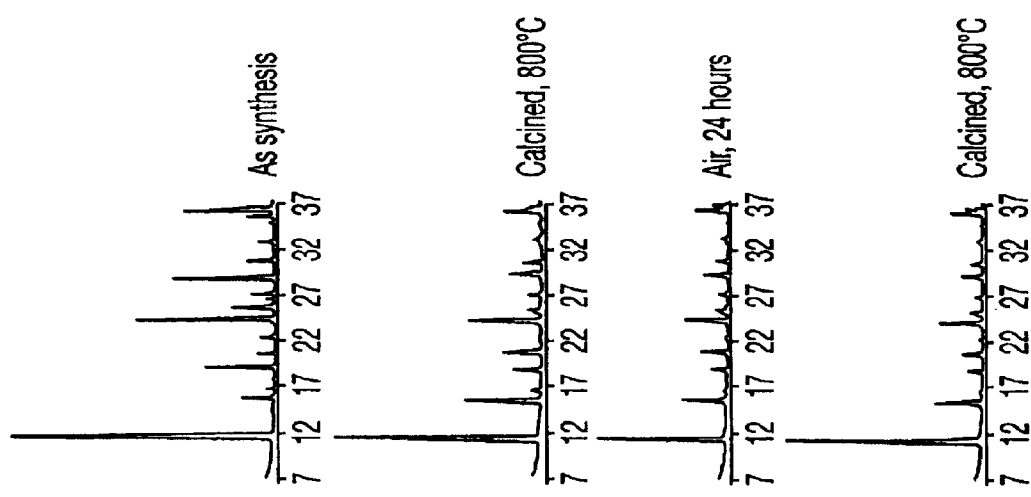
Figure 2. XRD-spectra of Example 1 sample

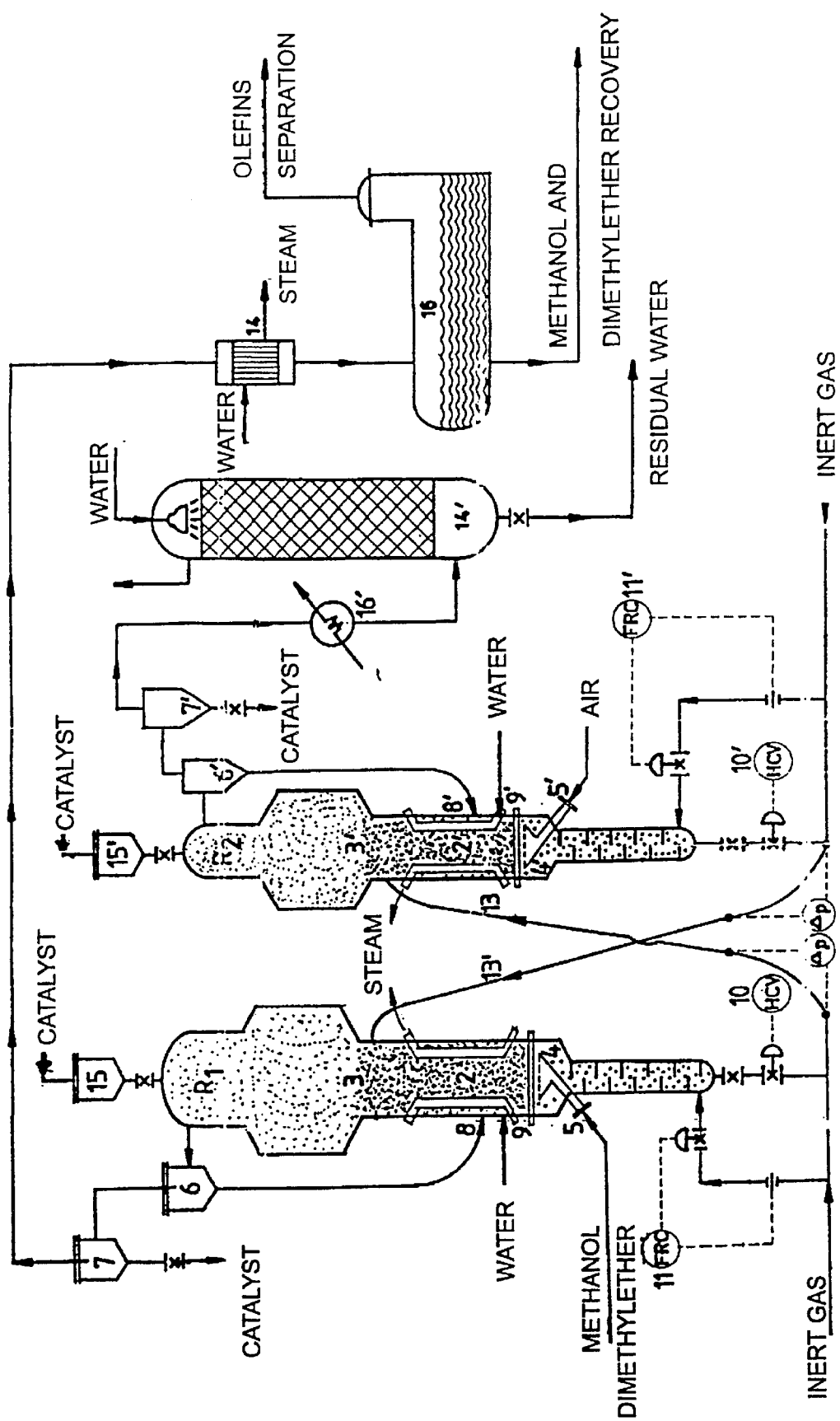
Figure 4. Installation for methanol conversion to olefins

CATALYTIC PROCESS FOR THE PREPARATION OF LIGHT OLEFINS FROM METHANOL IN FLUIDIZED BED REACTOR

This is a National Stage entry under 35 U.S.C. § 371 of Application No. PCT/RO99/00001 filed Jan. 11, 1999, and the complete disclosure of which is incorporated into this application by reference.

BACKGROUND OF THE INVENTION

1. Field of Invention

This invention relates to a process for conversion of methanol to olefins using SAPO-34 zeolite in fluidized bed reactor with continuous regeneration of catalyst.

2. Background Art of the Invention

Light olefins, namely ethylene and propytene, are important raw materials for polymers production.

Industrial, ethylene and propylene are obtained by steam cracking of $C_2$–$C_4$ paraffins and petroleum fractions in so called hydrocarbons pyrolisis process. The continuous rising of olefins requirement with the oil reserve shortage in the future make interesting the researches for new olefins manufacture technologies from non petroleum raw materials.

One of the more attractive method for $C_2$–$C_4$ olefins production is based on catalytic conversion of methanol because methanol is manufactured in advanced technologies with very high capacity till 800,000 mt/year a single line and has wide raw materials availability like natural gases including methane, coals and renewable biomass.

Methanol conversion into light olefins with industrial accepted yields was possible only after the synthesis of high silica zeolite ZSM-5 by Mobil Oil's researchers (U.S. Pat. No. 3,702,886). After this many other types of zeolites were tested in the reaction of methanol to olefins like ZSM-34 (U.S. Pat No. 4,079,096), Mordenite (Ro Patent 87685, U.S. Pat No. 3,244,766), Offretite (U.S. Pat No. 4,079,096) arseno-silicates (Ger. Off. 2830830), boro-silicates (Ger. Off. 2830787). Methanol conversion to olefins is claimed also in many patents based on synthtetic alumino-silicates like U.S. Pat Nos. 4,062,905, 3,979,472, 3,911,041 and Ger. Off. 2755299, 2615150.

These catalysts exhibit low selectivities in olefins and must be periodically regenerated with air at 470–570° C.

Numerous methods for modification of zeolites and reaction conditions were elaborated for olefins selectivity rising and increasing the active cycle of the catalysts. Interesting results were obtained by zeolite silification (U.S. Pat. Nos. 4,100,219, 4,145,315), increasing Si/Al atomic ratio by aluminium extraction (U.S. Pat. No. 4,447,669, Ger. Off. 2935863), ionic exchange or impregnation with Cs, Ba, Pb, TI (U.S. Pat No. 4,066,714), B, Mg (U.S. Pat No. 4,049,573, Ger. Off. 3300892), Hf, Zr (U.S. Pat No. 4,481,376, Ger. Off. 3300982), dilution of the catalyst with inert materials (U.S. Pat No. 4,025,572), partial deactivation with steam (UK Patent 2127036) or HF (U.S. Pat. No. 4,486,617). Good results have given complex treatments with Mg—Mg or Mg—Sb (RO Patent 87413). Some reaction parameters were also modified, for instance under atmospheric pressure utilization (U.S. Pat No. 4,025,575), steam dilution of feed (U.S. Pat No. 4,083,889) or dilution with air (U.S. Pat No. 4,433,189), oxygen (U.S. Pat. No. 4,049,735) and aldehyde (U.S. Pat No. 4,374,295). The synthesis by Union Carbide Corporation's researchers of Si—Al—P zeolites named SAPO-zeolites (U.S. Pat Nos. 4,310,440, 4,440,871) has opened new perspectives for methanol conversion to olefins, MTO-process. As the Chinese researchers have demonstrated for the first time onto SAPO-34 zeolite it obtained till 89% $C_2$–$C_4$ olefins at practical total conversion of methanol 57–59% being ethylene and ethylene/propylene molar ratio 2.24–2.31 (Applied Catalysis, Vol. 40, Nr. 1–2, 1988, p.316). Due to the catalyst coking active cycle is only 1–2 hours.

The use of SAPO-34 zeolite synthesised as in U.S. Pat No. 4,440,871 rose contradictory literature data concerning the thermal and steam stability and olefins selectivity. It must be also underlined that the sythesis of the zeolite is made with expensive materials like aluminium isopropoxyde, tetraethylammmonium hydroxide or quinuclydine. Neutralization of the reaction mixture with NaOH has complicated the technology for SAPO-34 manufacture due to the necessity of ammonium ion exchange and supplementary calcination step.

Thermal analysis (Gr.Pop et al., Progress in Catalysis, Bucharest, 1, 1993, p.1) showed that a good thermal and steam stability have SAPO-34 zeolites with crystals smaller than 4 micrometer.

MTO—process was materialized in tubular reactors with fixed bed catalyst (U.S. Pat No. 4,590,320) and in fluidized bed reactors with catalyst regeneration in fluidized bed. Vaporized methanol feed mixed with the zeolite catalyst is charged to the bottom of the riser contact zone to form a suspension for flow up wardly through the riser (U.S. Pat. No. 4,328,384). The reactors with fixed bed catalyst have many desadvantages in methanol reaction to olefins because the remove of the reaction heat is dificult and frequent catalyst regeneration diminishes production capacity. The increasing the coke deposits on the catalyst in the active cycle changes continuous the reaction products composition.

Fluidized bed reactors and continuous regeneration of the catalyst eliminate these desadvantages but in a riser reactor the optimal raction conditions can't be realized.

Kinetic studies in fluidized bed reaction have shown the maximum ethylene formation at short reaction time of about two seconds. (C. Tsakiris et al., Proc. IFAC Symposium DYCORD 92 College Park, Md., April 1992), which is not obtainable in a riser reactor. In a riser type reactor two important reaction paramiters, contact time and temperature, determining product selectivites can't be well controlled.

All as synthesized zeolite including SAPO-34, have low selectivity in methanol conversion to olefines. By zeolite modifications its selectivity can be increased. For example, PCT/US96/19673 teaches a process in which a SAPO-34 zeolite is modified by ion exchange with Ni and then given a catalyst with 30% more selective in methanol conversion into ethylene+propylene.

SUMMARY OF THE INVENTION

In the U.S. Pat. No. 5,095,163, SAPO-34 catalyst is hydrothermally treated 3–50 hours, in air or steam, at 650–775° C., the catalyst acidity decreases from about 5.2 meq.$NH_3$/cc 11.8 mez.$NH_3$/cc and selectively to $C_2$+$C_3$ olefines in methanol conversion increase from 63 to 80%. U.S. Pat. No. 4,873,390 uses a selective cocking of the SAPO-34 zeolite till 5–30% coke in the catalyst to improve the methanol transformation in ethylene from 6.04% to 46.65% and in propylene from 15.43% to 50.60%. Maximum ethylene+propylene selectively obtained is 83.7%.

The Invention eliminates these difficulties since the catalyst is obtained from cheap raw materials like industrial alumina and aqueous silica sol and the template, tetraethylammonium phosphate is "in situ" preparated: by ethylbromide and triethylamine. The methanol conversion and continuous catalyst regeneration are conducted in fluidized bed reactors, without riser, methanol feed being injected in dense bed catalyst.

The claimed process may find applications in the industry to obtain, by a new route more economic, ethylene and propylene, basic raw materials for petrochemistry and synthetic fuels.

BRIEF DESCRIPTION OF THE DRAWINGS

FIG. 1 shows a SEM microphotography of Example 1 zeolite.

FIG. 2 shows a XRD-spectra of Example 1 sample.

FIG. 3 shows dimension distribution curves of the catalyst of Example 1.

FIG. 4 shows an installation for methanol conversion to olefines.

DETAILED DESCRIPTION OF THE INVENTION

The catalyst synthesis made only with cheap, industrial raw material namely triethylamine, ethyl bromide, concentrated phosphonic acid, more than 70 weight %, hydrated alumina and silica sol, all with very low, under 0,01% Na content. Concentrated silica sol can be stabilized with ammonia. In the condition of the patent, by hydrothermal treatment of Si—Al—P amorphous gel is obtained the active, H form of SAPO-34 zeolite, in relatively short zeolitization time. After the calcination at 350–580° C. for remove the organic template, the obtained zeolite is used as catalyst. The zeolite is atomized at 400–450° C. in a silica matrix as microspheres. The compozition of amorphous gel and the reaction condition in the crystallization, calcination and atomization steps assure to obtain an active and selective catalyst for methanol conversion to olefins, with a granulation curve suitable in a fluidized bed process and with good thermal and mechanical resistance.

The process of methanol conversion to light olefins mainly ethylene and propylene, is realized in fluidized bed, including a reactor—regenerator system, with continuous circulation of the coked catalyst from reactor to regenerator and the regenerated catalyst form regenator to reactor. The methanol feed and regeneration air are injected in the dense bed of the catalyst. This system assures constant temperature in the catalyst beds and contact time of about two seconds. The reactor and regenerator risers only hinder the fluxes reversing. By steam or nitrogen purging in the risers, the catalyst is purified by the methanol and hydrocarbons adsorbed in reactor and oxygen adsorbed in regenerator. So the loss of methanol by burning in a regenerator is avoided. Also is avoided the burning of the methanol in the reactor by the oxygen adsorbed on the catalyst in regenerator. The purging of the catalyst assures a very low carbon oxydes in the reaction products with a supplementary reduction of the costs for olefins separation. To keep constant the catalyst activity a small amount is removed from reactor or regenerator in parallel with adding an equal quantity of fresch catalyst. The reactor and regenerator have interior devices for taking-over the heat reactions of methanol conversion and coke burning.

The following examples illustrate, but not limit, the present invention.

EXAMPLES

Example 1

By known method is prepared a tetraethylammonium phospate, aqueous solution 25%, from triethylamine, ethylbromide and phosphoric acid 73%.

Hydrated alumina 65% $Al_2O_3$ with 40% bayerite, is suspended in demineralized water and is charged, under stirring in a 3500 l autoclave over tetraethylammonium phosphate solution and then is added the 28% $SiO_2$ silica sol stabilized wih ammonia. Th pH of resulted suspension is fixed at 6.3–6.5 with phosphonic acid.

Molar ratio of the component in the suspension is:

$P_2O_5:Al_2O_3:SiO_2:TEAOH$ 1:1.5:0.37:1.1.

Zeolitization is made in six succesive steps: the first step of the cristallization begins with 15% of the whole suspension at 198–205° C. After 20 hours the autoclave is cooled at 30–40° C. and a new quantity of suspension is added. The zeolitization process is resumed in the same conditions. The operation is repeated five times. The entire zeolitization process, including intersteps cooling, is about 100 hours.

Analytical control, by XRD technique, of the product obtained shows more than 90% SAPO-34 zeolite and about 7% unreacted bayerite.

In Table 1 are shown the characteristic bands in the XRD—spectrum of the SAPO-34 zeolite obtained, and SAPO-34 spectrum reported in U.S. Pat. No. 4,440,871, for comparison.

TABLE 1

Characteristic bands in XRD-spectrum
(Cu lamp, Cu $k_\alpha$ = 1.5418)

| U.S. Pat. No. 4440871 | | | Sample, Example 1 | | |
|---|---|---|---|---|---|
| 2θ | d, Å | 100 Xi/$l_o$ | 2θ | d, Å | 100 Xi/$l_o$ |
| 9.45–9.65 | 9.36–9.17 | 81–100 | 9.63 | 9.18 | 100 |
| 12.8–13.05 | 6.92–6.78 | 8–20 | 12.87 | 6.88 | 18 |
| 13.95–14.20 | 6.35–6.24 | 8–23 | 14.17 | 6.25 | 21 |
| 16.0–16.2 | 5.54–5.47 | 25–54 | 16.16 | 5.4 | 47 |
| 17.85–18.15 | 4.97–4.89 | 11–26 | 18.3 | 4.89 | 22 |
| 19 | 4.67 | 0–2 | — | — | — |
| 20.55–20.9 | 4.32–4.25 | 44–100 | 20.67 | 4.3 | 97 |
| 22.05–22.50 | 4.03–3.95 | 0–5 | 22.33 | 3.98 | 4 |
| 23.0–23.15 | 3.87–3.84 | 2–10 | 23.15 | 3.84 | 8 |
| 24.95–25.4 | 3.57–3.51 | 12–87 | 25.38 | 3.52 | 26 |
| 25.8–26.0 | 3.45–3.43 | 14–24 | 25.97 | 3.43 | 17 |
| 27.5–27.7 | 3.243–3.220 | 1–4 | 27.68 | 3.22 | 4 |
| 28.05–28.4 | 3.181–3.143 | 1–12 | 28.4 | 3.14 | 4 |
| 29.2–29.6 | 3.058–3.018 | 3–9 | 29.15 | 3.06 | 4 |
| 30.5–30.7 | 2.931–2.912 | 19–75 | 30.67 | 2.91 | 29 |
| 31.05–31.4 | 2.880–2.849 | 15–28 | 31.25 | 2.86 | 22 |
| 32.2–32.4 | 2.780–2.763 | 1–5 | 32.42 | 2.76 | 3 |
| 33.4–33.85 | 2.683–2.648 | 0–6 | 33.66 | 2.66 | 4 |
| 34.35–34.65 | 2.611–2.589 | 4–15 | 34.48 | 2.6 | 7 |
| 36.0–36.5 | 2.495–2.462 | 2–11 | 36.33 | 2.47 | 4 |
| 38.8–38.9 | 2.321–2.315 | 0–2 | 38.8 | 2.32 | 2 |
| 39.6–39.7 | 2.276–2.070 | 2–4 | 39.76 | 2.27 | 5 |

The crystallite dimensions are between 1 and 3 micrometer (FIG. 1). The zeolite is stable by calcination and in air and steam, as is shown in FIG. 2.

In the zeolitization phase results a zeolite suspension with 16.7% solid wich is separated with 6.7 l/m² hours filtration rate. After washing with demineralized water and air drying results a paste of zeolite with 57% humidity.

The humid paste of zeolite is mixed with 28% $SiO_2$ Silica sol stabilized with ammonia in weight ratio zeolite: $SiO_2$ 60–40, fixed at pH 6.3 with nitric acid 40% and atomized under pressure with 400–450° C. hot air at entrance and 175–180° C. at exit. Injection pressure is 4–4.5 bars and the productivity of atomizer 50 kg/hour dry catalyst. Finaly the catalyst is calcined with a heating rate of 100° C./min. at two constant level, three hours at 350–400° C. and ten hours at 580° C. The cooling time of the catalyst is 4 hours. All the raw material used for catalyst preparation have a Na content under 0,01%. The microspherical catalyst obtained has good flow preperty and granulation curve showed in FIG. 3.

FIG. 4 is a schematic flow chart of the reaction—regeneration with fluid bed catalyst system for methanol conversion to olefins, MTO process, part of invention. With reference to FIG. 4, the reactor R1 is filled with 100 I catalyst and the regnerator R2 with 30 I catalyst. By fluidization is taked form the dense fluid bed catalyst 2–2' and upper interface 3–3'. The temperature of dense fluid bed catalyst in R1 is fixed at 440° C. and in R2 at 480–610° C. The temperatures in R1 and R2 are controlled by circulating heatin—cooling agent in interior heat exchangers 9–9'. Methanol and regenerating air are fed through connection 5–5' and sieves 4–4' with 100 l/hour respectively 1000 Nl/hour.

The circulation of the catalyst between reactor and regenerator is realized by nitrogen as lift gas through transfer lines 12–12'. Automatic control level of catalyst bed in R1 and R2 is made by keep constant the pressure drops with regulators 11–11', which act the catalyst flow rate regulating valves 10–10'. Reaction products and catalyst entrained are evacuated at the top of R1 and R2 and separated in cyclone systems 6–7 and 6'–7'. Through the conduits 8–8' the entrained catalyst is recycled in the reactor-regenerator reaction zone. About 2 kg catalyst is withdrwn from the bottom of separation cyclone 7 or 7' in each 48 hours and is replaced with the same quantity of fresh catalyst through the charge device 15 or 15'. So the irreversible desactivation of the catalyst is compensated.

The coked catalyst in the conduite 13 has 4.3 wt. % coke and the regenerated catalyst in conduite 13' has a coke retention level of 1.7 wt. %. Reaction products after the exit from cyclone 7 are cooled in heat exchanger 14 and separated in the separation vessel 16 into a noncondensed hydrocarbon fraction and a liquid fraction wich contains the process water, dimethylether and unconverted methanol. The gaseous hydrocarbon fraction is sent to a conventional olefins separation unit. From liquid fraction is separated by distillation dimethyleter and methanol wich are recycled to the reactors $R_1$.

Regeneration gases after cooling in heat exchanger 16' and washing in the column 14' are evacuated in the atmosphere.

The composition of the fluxes are shown in Table 2.

TABLE 2

Effluent composition obtained in Example 1.

| Component | Uncondensed organic phase vessel 16 wt. % | Liquid phase vessel 16 wt. % | Regeneration gases, exit cyclone 7' wt. % |
|---|---|---|---|
| Oxygen | — | — | 1.5 |
| Nitrogen | — | — | 82.7 |
| Carbon monoxyde | — | — | 4.3 |
| Carbon dioxyde | — | — | 11 |
| Hydrogen | 0.2 | — | 0.5 |
| Methane | 1.6 | — | — |
| Ethane | 0.3 | — | — |
| Ethylene | 46.8 | — | — |
| Propane | 2.5 | — | — |
| Propylene | 40 | — | — |
| Butanes | 0.53 | — | — |

TABLE 2-continued

Effluent composition obtained in Example 1.

| Component | Uncondensed organic phase vessel 16 wt. % | Liquid phase vessel 16 wt. % | Regeneration gases, exit cyclone 7' wt. % |
|---|---|---|---|
| 1-Butene | 1.74 | — | — |
| iso-Butene | 0.71 | — | — |
| 2-Butenes | 4.04 | — | — |
| $C_5$ + hydrocarbons | 1.58 | — | — |
| Methanol | — | 0.5 | — |
| Dimethylether | — | — | — |
| Water | — | 99.5 | — |

Example 2

Using the catalyst and installation of Exemple 1 by temperature and space velocity modification the ethylene/propylene ratio is changed in relatively large limits of 0.69–1.29.

Some illustrating results are shown in Table 3.

TABLE 3

Reaction products compositions, in different reaction conditions.

| | Experience number | | | | | |
|---|---|---|---|---|---|---|
| | 1 | 2 | 3 | 4 | 5 | 6 |
| a. Reaction conditions | | | | | | |
| Temperature, ° C. | 400 | 405 | 410 | 435 | 470 | 490 |
| LHSV, $h^{-1}$ | 1.1 | 0.6 | 1 | 1.9 | 1.5 | 2.7 |
| b. Un-condensed organic phase analysis, wt. % | | | | | | |
| Hydrogen | 0.08 | 0.23 | 0.13 | 0.12 | 0.71 | 0.1 |
| Carbon oxydes | — | — | — | 0.14 | 0.21 | — |
| Methane | 0.62 | 1.78 | 0.81 | 1.12 | 2.42 | 0.91 |
| Ethane | 0.26 | 0.9 | 0.42 | 0.64 | — | — |
| Ethylene | 28.3 | 48.5 | 34.1 | 43 | 42.45 | 36.8 |
| Propane | 2.3 | 5.3 | 2.4 | 2.43 | 5.9 | 2.27 |
| Propylene | 41.2 | 35.7 | 42.9 | 42 | 32.95 | 45.4 |
| Butanes | 0.9 | 0.88 | 0.8 | 0.68 | 0.8 | 0.72 |
| 1-Butene | 1.94 | 1.19 | 1.75 | 1.63 | 1.94 | 1.7 |
| iso-Butene | 0.77 | 1.23 | 0.75 | 0.44 | 1.04 | 0.2 |
| 2-Butenes | 7.22 | 2.56 | 6.68 | 4.87 | 7.13 | 5.2 |

REFERENCES

1. Brent M. Lok, Celeste M. Messina, Robert L. Pation, Richard T. Gajek, Thomas R. Cannan, Edith M. Flanigen (Union Carbide Corporation), U.S. Pat. No. 4,440,871 (Apr. 3, 1984), Int. Cl. B01 j 27/14; U.S. Cl 502/241.
2. Ajit V. Sapre (Mobil Oil Corporation), U.S. Pat. No. 4,590,320 (May 20, 1986), Int. Cl. Co7C1/20; U.S. Cl.585/324; 585/315
3. Nicholas Davidiuk, James Haddad (Mobil Oil Corporation) U.S. Pat. No. 4,328,384 (May 4, 1982), Int. Cl. C 97c1/20, U.S. Cl. 585/469; 585/639; 585/733.

|  | Experience Number | | | | | |
| --- | --- | --- | --- | --- | --- | --- |
|  | 1 | 2 | 3 | 4 | 5 | 6 |
| C$_5$ + Hydrocarbons | 2.41 | 0.95 | 2.84 | 1.58 | 4.45 | 1.75 |
| Dimethylether | 14.00 | 0.78 | 6.42 | 1.35 | — | 4.95 |
| c. Liquid phase analysis, wt. % | | | | | | |
| Dimethylether | 1.5 | — | 0.5 | — | — | — |
| Methanol | 12 | 3 | 9 | 1.5 | 0.1 | 1.5 |
| Water | 86.5 | 97 | 90.5 | 98.5 | 99.9 | 98.5 |
| d. Coke deposits on the catalyst, wt. % | | | | | | |
| Reactor R$_1$ exit | 4.9 | 5 | 4.8 | 4.5 | 4.6 | 4.7 |
| Regenerator R$_2$ exit | 1.2 | 2.8 | 0.6 | 0.9 | 1.2 | 1.9 |
| e. Ethylene/propylene ratio | 0.69 | 1.36 | 0.79 | 1.02 | 1.29 | 0.81 |
| f. Methanol conversion | 93.3 | 98.3 | 95 | 99.2 | 100 | 99.2 |

What is claimed is:

1. A method for the preparation of light olefins from methanol conversion using a microspherical catalyst comprising SAPO-34 zeolite, and the method comprising the step of contacting methanol with a fluidized or moving bed of said catalyst and being characterized in that said SAPO-34 zeolite is prepared from alumina, silica and a preformed template tetraethylammonium phosphate.

2. A method according to claim 1 comprising the further steps of:

continuously regenerating the catalyst of said bed with air, and substituting a portion of regenerated catalyst with fresh catalyst in order to keep constant the activity and selectivity of the catalyst.

3. A method according to claim 2, in which the regeneration with air is performed at 480–610° C.

4. A method according to claim 2, in which the contacting and the regeneration steps are performed in a reactor and a regenerator respectively with continuous circulation of the catalyst between said reactor and said regenerator.

5. A method according to claim 1, in which methanol is contacted with said catalyst at a temperature of 400–490° C. and liquid space velocities of 0.6 to 2.7 h$^{-1}$.

6. A method according to claim 1, in which the preformed template tetraethylammonium phosphate is prepared from triethylamine, ethylbromide and phosphoric acid.

7. A method according to claim 1 in which the microspherical catalyst is obtained by the steps of:

atomizing a mixture of said SAPO-34 zeolite and silica under pressure and at 400–450° C. to form microspheres.

* * * * *